(12) United States Patent
Srinivasan et al.

(10) Patent No.: US 6,828,808 B2
(45) Date of Patent: Dec. 7, 2004

(54) LONG-LIFE CONDUCTIVITY SENSOR SYSTEM AND METHOD FOR USING SAME

(75) Inventors: Rengaswamy Srinivasan, Ellicott City, MD (US); Francis B. Weiskopf, Jr., Catonsville, MD (US); Kenneth R. Grossman, Olney, MD (US); Russell P. Cain, Columbia, MD (US); Hassan Saffarian, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 3 days.

(21) Appl. No.: 10/344,000
(22) PCT Filed: Jul. 10, 2001
(86) PCT No.: PCT/US01/21739
§ 371 (c)(1),
(2), (4) Date: Feb. 6, 2003
(87) PCT Pub. No.: WO03/006958
PCT Pub. Date: Jan. 23, 2003

(65) Prior Publication Data
US 2004/0124858 A1 Jul. 1, 2004

(51) Int. Cl.[7] .......................... G01R 27/08; G01N 27/02
(52) U.S. Cl. ........................................ 324/693; 324/439
(58) Field of Search ................................ 324/693, 439, 324/441–444, 450, 691, 694–696, 663; 702/50; 73/335.05

(56) References Cited

U.S. PATENT DOCUMENTS 6,057,693 A * 5/2000 Murphy et al. ............. 324/663
6,223,129 B1 * 4/2001 Chan et al. ................... 702/30

FOREIGN PATENT DOCUMENTS

| DE | 35 11706 | 10/1986 |
|---|---|---|
| DE | 35 17772 | 11/1986 |
| WO | WO 88/09498 | 12/1988 |
| WO | WO 99/58990 | 11/1999 |

OTHER PUBLICATIONS

PCT International Search Report, PCT/US01/21739, Mailed Apr. 16, 2002.

* cited by examiner

Primary Examiner—Anjan Deb
Assistant Examiner—Amy He
(74) Attorney, Agent, or Firm—Albert J. Fasulo, II

(57) ABSTRACT

A long-life conductivity sensor system and method that is embeddable or immersible in a medium. The conductivity sensor system includes at least a housing with an enclosing wall that defines an interior volume and that has at least one aperture through the wall; a pair of electrodes protruding through the aperture into a medium surrounding the sensor housing; and conductivity sensing electronics contained within the sensor housing interior volume and connected to the pair of electrodes. The conductivity sensing electronics include a galvanostat connected to the electrodes for inducing discrete constant current pulses between the electrodes creating a transient voltage signal between the electrodes; and a high-speed voltmeter/A-D Converter connected to the electrodes for measuring the transient voltage signal between the electrodes, the transient voltage signal being a function of the conductivity of the medium surrounding the sensor housing.

25 Claims, 2 Drawing Sheets

LONG-LIFE CONDUCTIVITY SENSOR SYSTEM AND METHOD FOR USING SAME

FIELD OF THE INVENTION

The present invention relates generally to monitoring the conductivity of a medium. More particularly, the present invention is directed to a long-life conductivity sensor system and method for monitoring the conductivity of a medium, such as concrete, by embedding or immersing a sensor within the medium.

BACKGROUND OF THE INVENTION

Long-term monitoring of conductivity is often important in mediums such as concrete, soil and fluids. Steel is widely used in reinforcing concrete in buildings, bridges and roads. The conductivity of concrete can be used as a measure of corrosion of the steel. The electrical conductivity of concrete is usually low; however if concrete is contaminated with salt, then the conductivity of concrete will increase. And salt—more specifically, the chloride in salt—can cause the reinforcing steel to corrode. The steel reinforcement bars embedded in the concrete inherently have anodes and cathodes on the same surface, and the concrete acts as an electrolyte. Together, the anodes, cathodes and the electrolyte behave much like a short-circuited battery. This electrochemical process causes corrosion of the anodic areas of the steel, leaving the cathodic areas intact. If the concrete has been contaminated with chloride, the conductivity of the concrete will increase, which will accentuate corrosion, and eventually destroy the steel.

The conductivity of soil is a useful parameter in agriculture because conductivity correlates generally to soil grain size and texture: sands have a low conductivity, and silts have a medium conductivity. Clay can have a high or low conductivity, depending upon its mineral content. Conductivity in shale and bedrock can vary with season due to flooding and water entrapment. Soils that have moderate conductivity, are medium textured, and have medium water-holding properties are often the most agriculturally productive. Furthermore, long-term soil conductivity data can be used to estimate the corrosion rates of buried metal pipelines and metal conduits. Such data can also provide an indication of leaks and plumes originating from storage tanks and waste management areas, and contamination/pollution in soil sub-surfaces.

Many scientific disciplines require accurate, long-term monitoring of the conductivity of fluids. Environmentalists generally use conductivity data to determine seasonal changes in the salinity of lakes and oceans. Chemical engineers are able to use conductivity data to monitor corrosion rates in large holding tanks and industrial equipment.

The conductivity data in all of the above examples are generally obtained using one of two types of conductivity sensors. One type is the inductive sensor, and the other is the electrode sensor. The inductive-type conductivity sensor uses a toroidal input transformer to induce a voltage in an electrolyte medium. A toroidal output transformer measures the induced current, which is a function of the conductivity of the medium. Because of the nature of transformers, this type of conductivity sensor is relatively large and is less common than the electrode-type conductivity sensor.

Electrode-type conductivity sensors are further divided into sensors with two electrodes and sensors with four electrodes. In the two-electrode sensors, generally, a current (I) is induced between the two electrodes by applying a potential or voltage difference (from an external power source) between those electrodes. The voltage difference ($\Delta V$) and the current are measured and recorded. The ratio of voltage difference to current ($\Delta V/I$) provides the resistance from which the conductivity ($\kappa$) is computed as follows:

$$\kappa = k(I/\Delta V) \qquad \text{(Eq. 1)}$$

where k is the cell constant with units of $cm^{-1}$ or $m^{-1}$, and $\kappa$ is conductivity with units of $ohms^{-1}\ cm^{-1}$, $ohm^{-1}\ m^{-1}$, $mho\ cm^{-1}$, $mho\ m^{-1}$, $S\ cm^{-1}$ or $S\ m^{-1}$. The value of k is determined for each pair of sensors using a medium of known conductivity.

The four-electrode conductivity sensors employ a second pair of electrodes. The first pair of electrodes passes a constant current between them and through the medium. The second pair of electrodes measures the voltage difference between two points in the medium through which current is passing. For example, a constant current is applied across two outer electrodes, and the conductivity of the medium surrounding the electrodes is then calculated using the values of the voltage drop across two inner electrodes, the applied current, and the cell constant.

Prior art electrode-type conductivity sensors are widely adopted for spot-checking conductivity values and for short-term, in-line, and in-situ measurements. Existing applications include various types of industrial and environmental monitoring. However, a disadvantage of the prior art conductivity sensors of both the inductive type and the electrode type is that they have not been capable of long-term, in-situ monitoring across a wide range of conductivity values.

A prior art corrosion sensor intended for long-term, in-situ measurement in reinforced concrete is described in U.S. Pat. No. 5,895,843, issued Apr. 20, 1999, to Taylor et al. (the '843 patent). It measures changes in the resistance in a steel wire that is buried in the concrete but not connected to the rebar steel reinforcement. The wire is the sensor: corrosive agents entering the concrete corrode the wire, thinning the wire and changing its resistance. This is an indirect method to infer corrosion of the rebar. Rather than monitoring the conditions including high conductivity that will eventually result in rebar corrosion, the method described in the '843 patent detects corrosion only after damage to the wire, and by inference, damage to the rebar has occurred. Remedial action to correct a corrosive environment is likely to be more effective if taken early. Such early action is possible only if an environment is monitored directly, rather than simply detecting after-the-fact the deleterious results.

Finally, the voltage applied across the electrodes of an electrode-type conductivity sensor can introduce errors in the conductivity measurement. The conductivity of a medium is based on ion mobility. When a DC voltage is applied across the electrodes of a conductivity sensor, the ions near the electrodes are quickly depleted and the electrodes become polarized. Such polarization results in measurements that are higher than the actual resistance between the electrodes. Techniques using AC voltage have been developed to overcome this problem (see, for example, U.S. Pat. No. 4,751,466, issued Jun. 14, 1988, to Colvin et al.); however, such techniques employ complex AC waveforms that require sophisticated electronic components, which add to the cost and size of the corresponding sensor systems.

Therefore, particularly in the above-described areas of steel-reinforced-concrete, soil, and fluid monitoring, a need exists for a long-life conductivity sensor that may be permanently installed in a location, that reliably monitors conductivity changes over several orders of magnitude over a period of months or years, and that provides early warning of potential corrosion.

SUMMARY OF THE INVENTION

The present invention, among other things, presents a solution to the previously discussed disadvantages associated with prior art conductivity sensors.

It is an object of the present invention to provide a conductivity sensor system that may be embedded in solids such as concrete or soil, or immersed in fluids such as chemical reagents found in holding tanks, to monitor changes in conductivity over several orders of magnitude over long periods of time, up to several years.

Another object of the present invention is to provide a conductivity sensor system that is compact in size.

Yet another object of the present invention is to provide a conductivity sensor system that is of relatively low cost such that numerous conductivity sensors may be used in a single project, for example, embedded in a reinforced concrete bridge, while not significantly increasing the overall cost of the project.

Yet another object of the present invention is to provide a conductivity sensor system that overcomes the electrode polarization problems associated with some prior art conductivity sensors.

These and other objects are achieved in the present invention in a conductivity sensor system having at least a housing with an enclosing wall that defines an interior volume and that has at least one aperture through the wall; a pair of electrodes in contact with a medium surrounding the sensor housing; and conductivity-sensing electronics contained within the sensor housing interior volume and connected through the aperture in the wall to the pair of electrodes. The conductivity-sensing electronics include a galvanostat connected to the electrodes for inducing discrete, constant current pulses between the electrodes, creating a transient voltage signal between the electrodes; and a high-speed voltmeter/A-D converter connected to the electrodes for measuring the transient voltage signal between the electrodes, the transient voltage signal being a function of the conductivity of the medium surrounding the sensor housing.

Other objects and advantages of the invention will become more fully apparent from the following, more detailed description and the appended drawings, which illustrate several embodiments of the invention.

DETAILED DESCRIPTION OF THE INVENTION

Figure 1:
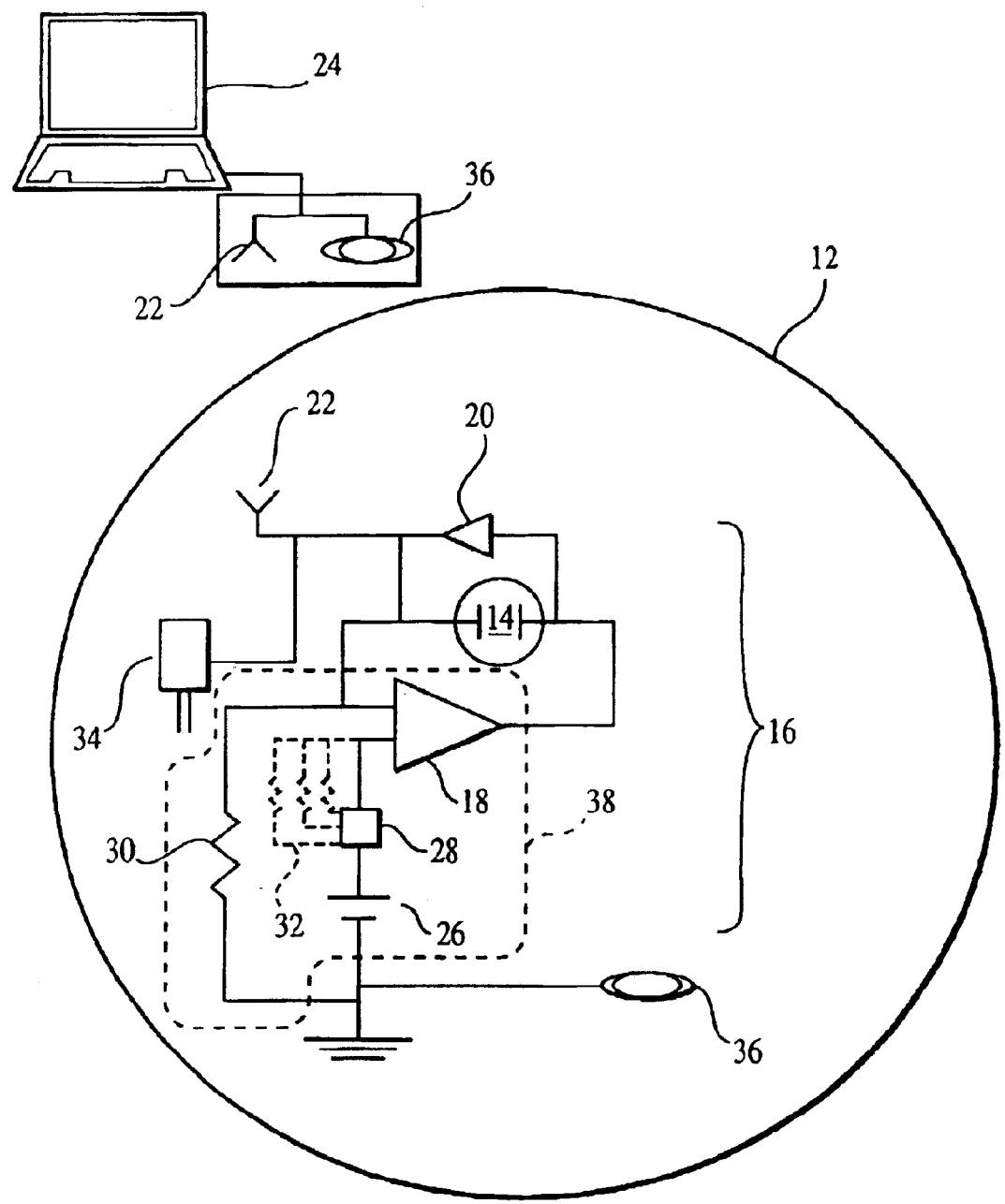
FIG. 1 is a schematic representation of a conductivity sensor system according to the present invention.
Figure 2A:
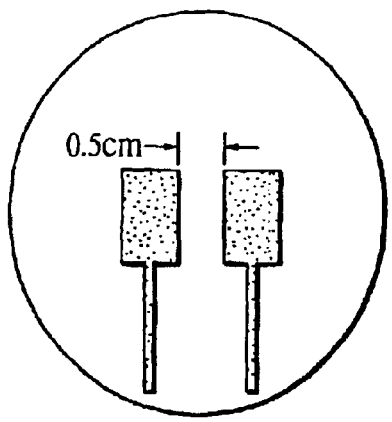
FIGS. 2A–2D show examples of several electrode designs according to the present invention.
Figure 2B:
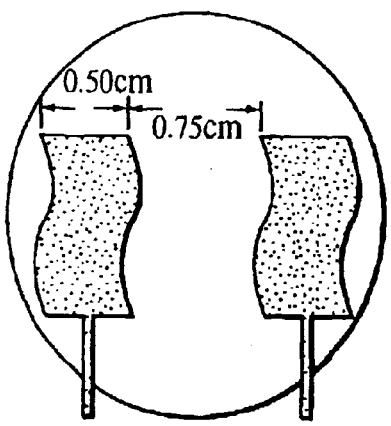
Figure 2C:
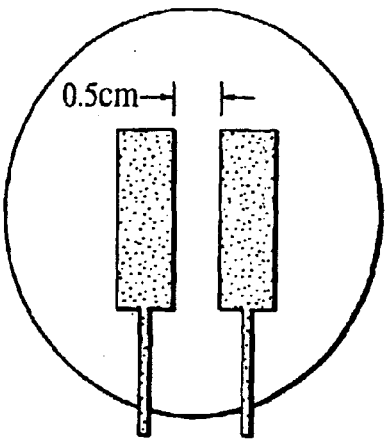
Figure 2D:
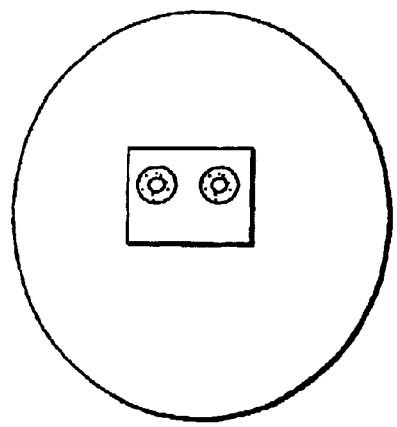

FIG. 1 is a schematic representation of a conductivity sensor system according to the present invention. The conductivity sensor system of the present invention includes at least housing 12 having at least two electrodes 14 operatively connected to the conductivity-sensing circuitry 16 enclosed within housing 12 and having at least a galvanostat 38 (a constant-current source) and a high-speed voltmeter/A-D converter 20. In general, the housing 12 will be formed from conventional materials known in the art. Suitable materials for use herein include, but are not limited to, ceramic materials, for example, alumina and macor; plastic materials; nylon; concrete; and epoxy and the like. As one skilled in the art would readily appreciate, dimensions and configurations for the housing 12 can vary as dictated by the application and can be determined on a case-by-case basis. However, employing a basic two-electrode design enables the size of the sensor housing 12 to be relatively compact.

The sensor electronics are arranged inside the housing 12 and the housing is sealed, for example, with chemically resistant epoxy. The electrodes 14 include typically a 10- to 100-micron-thick deposit of gold on alumina; however platinum, nickel, or other highly conductive materials may replace the gold. The electrodes are electrically connected to the electronics inside the housing 12 through an aperture in the wall of the housing 12.

A constant current is supplied across the electrodes 14 of the conductivity cell by the galvanostat 38. In one embodiment of the present invention, the galvanostat 38 consists of an amplifier 18, a resistor 30, a relay 28 and a power source 26 wired together as shown in FIG. 1. Relay 28 and resistor 30 provide overcurrent protection for the galvanostat 38, as known in the art. The high-speed voltmeter/A-D converter 20 is connected across the conductivity cell to measure the resulting potential between the electrodes 14. The voltage data are then outputted via a data link 22 to a processor 24, for example, a processor within a laptop computer.

The sensor circuitry and data link 22 are also powered by the power source 26 that may include a rechargeable nickel-cadmium or lithium-ion battery or a super capacitor. It is contemplated that the power source 26 can be internal to the sensor housing 12 when the sensor is embedded in concrete or soil, and external to the sensor housing 12 when the sensor is immersed in a fluid inside a chemical container or a tank. The power source 26 is linked to an external power source such as a battery for recharging the power source 26. The link can be either through an inductive coupling 36 or direct wire contacts.

The relay 28 may also be used to place optional shunt resistors 32 in parallel with the relay circuit. A combination of shunt resistors 32 may be selected to change the magnitude of the discrete constant-current outputs of the galvanostat 38. As described in the examples that follow, the ability to change the magnitude of the current output of the galvanostat 38 greatly increases the range of any given sensor design having a fixed conductivity cell constant.

Temperature can also vary the conductivity of the ambient medium by as much as 1–3% per degree C. Therefore the present invention may include an optional temperature probe 34 as part of the conductivity sensor circuitry. The voltage data from the temperature probe 34 is also transmitted through the data link 22.

The operator can determine the conductivity of the medium using the measured voltage across the electrodes 14, the applied current, the cell constant, and the measured temperature of the medium. Such calculations can also be automated in the processor 24. As described in the examples that follow, the actual level of voltage depends upon the details of the galvanostat 38 and the cell constant of the conductivity cell. By adjusting the distance between the electrodes 14, their shape, and their size, any cell constant can be produced. By varying the current, the sensor can be used in various mediums with different initial conductivity values.

Figure 3:
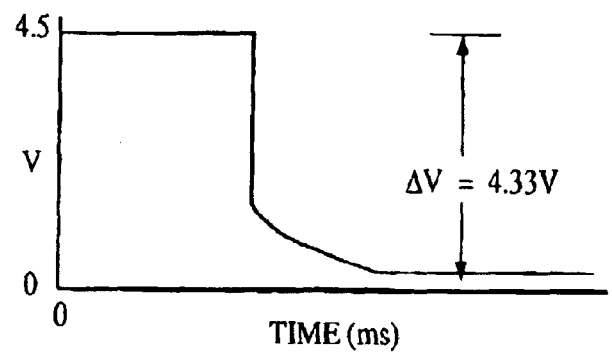
FIG. 3 illustrates a voltage transient between two electrodes.

The present invention minimizes the errors found in many prior art sensors caused by depletion of ions near the electrodes 14 and the resulting polarization of the electrodes 14. As described previously, these errors result in measurements that are higher than the actual resistance. The errors are minimized by employing a technique known as chronopotentiometry. The galvanostat 38 applies a very short, discrete current pulse, I, across the two electrodes 14. A typical duration of the pulse is less than 4 milliseconds, and its magnitude varies from 0 to I to 0. Because the pulse width is so short, ion depletion near the electrodes 14 and the resulting errors from electrode polarization are negligible. During and immediately after the pulse, the voltage across the electrodes 14 varies with time. This voltage transient is illustrated in FIG. 3. A high-speed voltmeter/A-D converter 20 measures the difference between the maximum voltage, which occurs when the pulse is applied, and the minimum voltage, which is present after the transient is fully attenuated. This $\Delta V$ is used to determine the conductivity using Eq. 1.

The following non-limiting examples are illustrative of the method for monitoring the conductivity of a medium over several orders of magnitude employing a conductivity sensor system in accordance with the present invention. In these examples, no physical access to or recalibration of the sensors is required.

EXAMPLES

Consider an embodiment of the present invention having a voltage-measuring device including an amplifier and a 12-bit A/D converter that operate between +3 and −3 V. The resulting maximum readable voltage is ±0.0015 V, and the resolution is 3 mV. During experimental measurements using this embodiment, the conductivity cells having the best performance consisted of two ring electrodes (14) having the following specifications: distance between the centers of the two rings=7.5 mm; ring OD=2.0 mm; ring ID=1.25 mm. FIGS. 2A–2D illustrate this embodiment and several other electrode designs according to the present invention. Now consider these limitations in conjunction with the formula used in computing conductivity ($\kappa$)

$$\kappa = k(I/\Delta V). \quad \text{(Eq. 1)}$$

Next consider a medium whose conductivity is assumed to change from 0.001 S cm$^{-1}$ to 0.1 S cm$^{-1}$; the corresponding resistivity changes from 1,000 to 10 ohm.cm. Such values can be expected in fresh water that is contaminated by saline water. In this case, a current of 375 microampere ($\mu$A) is applied across a cell with a cell constant ($\kappa$) of 8 cm$^{-1}$. The combination of 375-$\mu$A current and 8 cm$^{-1}$ cell constant will generate 3 V and 30 mV at 1,000 and 10 ohm.cm, respectively. These voltages are within the +3 V range and the 0.0015 V sensitivity of the 12-bit A/D converter.

Next consider the case of concrete, where the conductivity values could change from 3.3×10$^{-6}$ to 3.3×10$^{-4}$ S cm$^{-1}$. The corresponding resistivity changes from 300,000 to 3,000 ohm.cm. In this case, a current of 10 microampere is applied across a cell with a cell constant of 1 cm$^{-1}$. The combination of 10-$\mu$A current and 1 cm$^{-1}$ cell constant will generate 3 V and 30 mV at 300,000 and 3,000 ohm.cm, respectively. These voltages are again within the ±3 V range and the 3 mV sensitivity of the 12-bit A/D converter. In this fashion, embodiments of an embedded conductivity sensor according to the present invention may measure large changes in conductivity over several orders of magnitude without any need to access the embedded sensor physically.

In summary, the present invention provides for a long-life conductivity sensor system that is embeddable in solids such as concrete or soil, or immersible in fluids such as chemical reagents found in holding tanks, and that can reliably monitor conductivity changes in these environments over a period of months or years. Also, the sensors are compact and have a relatively low cost such that numerous sensors may be used in a single project, for example embedded in a reinforced concrete bridge, while not significantly increasing the overall cost of the project. Furthermore, different embodiments of the present invention are adaptable to conductivity monitoring in diverse mediums such as concrete, soil, and fluids and can measure large changes in conductivity over several orders of magnitude. While the above description contains many specifics, the reader should not construe these as limitations on the scope of the invention, but merely as examples of specific embodiments thereof. Those skilled in the art will envision many other possible variations that are within its scope. Accordingly, the reader is requested to determine the scope of the invention by the appended claims and their legal equivalents, and not by the specific embodiments given above.

What is claimed is:

1. A conductivity sensor system comprising:
   a sensor housing having an enclosing wall that defines an interior volume and that has an aperture through said wall;
   a pair of electrodes in contact with a medium surrounding said sensor housing; and
   conductivity sensing electronics contained within said sensor housing interior volume and operatively connected through said aperture to said pair of electrodes, said conductivity sensing electronics comprising:
      a galvanostat operatively connected to said electrodes for inducing a discrete constant current pulses between said electrodes creating a transient voltage signal between said electrodes; and
      a high-speed voltmeter/A-D converter operatively connected to said electrodes for measuring, between said electrodes, a difference between (i) a maximum of the transient voltage signal occurring during the induced current pulse, and (ii) a minimum voltage occurring after the induced current pulse when the transient voltage signal is fully attenuated, the transient voltage signal being a function of the conductivity of the medium surrounding said sensor housing.

2. The conductivity sensor system of claim 1 wherein the housing is a material selected from the group consisting of ceramic material, plastic material, nylon, concrete, epoxy and combinations thereof.

3. The conductivity sensor system of claim 1 wherein said galvanostat induces discrete constant current pulses having a duration less than 4 milliseconds.

4. The conductivity sensor system of claim 1 wherein said galvanostat induces discrete constant current pulses having different magnitudes.

5. The conductivity sensor system of claim 1 further comprising a temperature probe contained within said sensor housing and operatively connected to said conductivity sensing electronics for determining the temperature of the medium surrounding said sensor housing.

6. The conductivity sensor system of claim 1 wherein the conductivity sensing circuitry is powered by a power source.

7. The conductivity sensor system of claim 6 wherein the power source is inside or outside said sensor housing.

8. The conductivity sensor system of claim 6 wherein the power source is a battery or capacitor.

9. A method for monitoring the conductivity of a medium comprising the steps of:

providing a conductivity sensor system comprising a sensor housing having an enclosing wall that defines an interior volume and that has an aperture through said wall; a pair of electrodes protruding through said aperture into a medium surrounding said sensor housing; and conductivity sensing electronics contained within said sensor housing interior volume and operatively connected to said pair of electrodes, said conductivity sensing electronics comprising: a galvanostat operatively connected to said electrodes for inducing a discrete constant current pulses between said electrodes creating a transient voltage signal between said electrodes; and a high-speed voltmeter/A-D Converter operatively connected to said electrodes for measuring, between said electrodes, a difference between (i) a maximum of the transient voltage signal occurring during the induced current pulse, and (ii) a minimum voltage occurring after the induced current pulse when the transient voltage signal is fully attenuated, said transient voltage signal being a function of the conductivity of the medium surrounding said sensor housing; and, embedding said conductivity sensor system within the medium to be monitored.

10. The method of claim 9 wherein the medium is selected from the group consisting of concrete, soil, storage tanks containing chemical reagents or biological mediums.

11. The method of claim 9 wherein said sensor housing of the conductivity sensor system is a material selected from the group consisting of ceramic material, plastic material, nylon, concrete, epoxy and combinations thereof.

12. The method of claim 9 wherein said galvanostat induces discrete constant current pulses having a duration less than 4 milliseconds.

13. The method of claim 9 wherein said galvanostat induces discrete constant current pulses having different magnitudes.

14. The method of claim 9 wherein said conductivity sensor system further comprises a temperature probe contained within said sensor housing and operatively connected to said conductivity sensing electronics for determining the temperature of the medium surrounding said sensor housing.

15. The method of claim 9 wherein said conductivity sensing circuitry is powered by a power source.

16. The method of claim 9 wherein said power source is inside or outside said sensor housing.

17. The method of claim 9 wherein said power source is a battery or capacitor.

18. A conductivity sensor system comprising:

a sensor housing having an enclosing wall that defines an interior volume and that has an aperture through said wall;

a pair of electrodes protruding through said aperture into a medium surrounding said sensor housing;

current inducing means for inducing a discrete constant current pulse between said electrodes, said current inducing means contained within said sensor housing interior volume and operatively connected to said electrodes; and high-speed voltage measuring means for measuring, between said electrodes, a difference between (i) a maximum of the transient voltage signal occurring during the induced current pulse, and (ii) a minimum voltage occurring after the induced current pulse when the transient voltage signal is fully attenuated, said high-speed voltage measuring means contained within said sensor housing interior volume and operatively connected to said electrodes, the transient voltage signal being a function of the conductivity of the medium surrounding said sensor housing.

19. The conductivity sensor system of claim 18 wherein the housing is a material selected from the group consisting of ceramic material, plastic material, nylon, concrete, epoxy and combinations thereof.

20. The conductivity sensor system of claim 18 wherein said galvanostat induces discrete constant current pulses having a duration less than 4 milliseconds.

21. The conductivity sensor system of claim 18 wherein said galvanostat induces discrete constant current pulses having different magnitudes.

22. The conductivity sensor system of claim 18 further comprising a thermocouple probe contained within said sensor housing and operatively connected to said conductivity sensing electronics for determining the temperature of the medium surrounding said sensor housing.

23. The conductivity sensor system of claim 18 wherein the conductivity sensing circuitry is powered by a power source.

24. The conductivity sensor system of claim 18 wherein the power source is inside or outside said sensor housing.

25. The conductivity sensor system of claim 18 wherein the power source is a battery or capacitor.

* * * * *